United States Patent [19]

Hoelderich et al.

[11] Patent Number: 4,709,097

[45] Date of Patent: Nov. 24, 1987

[54] CONVERSION OF 1,3-DIOXANES TO 4-OXA-ALDEHYDES

[75] Inventors: Wolfgang Hoelderich; Franz Merger, both of Frankenthal; Rolf Fischer, Heidelberg, all of Fed. Rep. of Germany

[73] Assignee: BASF Aktiengesellschaft, Ludwigshafen, Fed. Rep. of Germany

[21] Appl. No.: 851,782

[22] Filed: Apr. 14, 1986

[30] Foreign Application Priority Data

Apr. 17, 1985 [DE] Fed. Rep. of Germany ....... 3513725

[51] Int. Cl.$^4$ ............................................. C07C 45/60
[52] U.S. Cl. ................................... 568/443; 568/427; 568/450; 549/498; 549/78; 546/340; 560/177; 560/262
[58] Field of Search ............... 568/427, 443, 450, 483; 549/497, 78; 546/340; 560/177, 262

[56] References Cited

U.S. PATENT DOCUMENTS

| 2,479,632 | 8/1949 | Lundsted et al. | 568/450 |
| 3,060,240 | 10/1962 | Hellin et al. | 568/483 |
| 4,324,921 | 4/1982 | Arpe | 568/427 |
| 4,599,458 | 7/1986 | Fischer et al. | 568/450 |

FOREIGN PATENT DOCUMENTS 2922698 12/1980 Fed. Rep. of Germany ...... 568/427

OTHER PUBLICATIONS

J. American Chem. Soc. 82 (1960), pp. 6419–6420.
Ibid., 84 (1962), pp. 3307–3326.

*Primary Examiner*—James H. Reamer
*Attorney, Agent, or Firm*—John H. Shurtleff

[57] ABSTRACT

4-oxa-aldehydes are prepared by catalytic isomerization of a 1,3-dioxane using an acidic zeolite catalyst.

15 Claims, No Drawings

CONVERSION OF 1,3-DIOXANES TO 4-OXA-ALDEHYDES

The present invention relates to a process for the preparation of 4-oxa-aldehydes by catalytic isomerization of 1,3-dioxanes.

It is known that 1,3-dioxane and its derivatives can be subjected to a rearrangement reaction to give β-alkoxyaldehydes (J. Amer. Chem. Soc. 82 (1960), 6419–6420 and ibid. 84 (1962), 3307–3319 and 3319–3326). The catalysts used here were silica gel and pumice, and these showed pronounced signs of deactivation. Furthermore, their activity and selectivity are not satisfactory from an economic point of view. Because the natural product pumice does not have a sufficiently specific composition and its composition is varied depending on origin, the reaction may be influenced by uncontrollable factors (Houben-Weyl, Methoden der organische Chemie, volume IV, 2, page 149 (1955)).

German Laid-Open Application DOS No. 2,922,698 describes a process for the preparation of β-alkoxypivaldehyde from a 1,3-dioxane using, as the catalyst, silica doped with hydroxides of groups III A and/or III B and an alkali metal hydroxide. These catalysts, which result in only slight progress, therefore differ from those described above in that the acidic centers are neutralized. Compounds of the pure lanthanides praseodymium and neodymium, which are required for producing the catalysts, are expensive and not readily available. The preferably used commercial lanthanide mixture didymium varies in its composition, so that the industrial catalysts are difficult to reproduce. The stated catalyst lives are only of the order of hours, and no information is given concerning regeneration of the catalysts.

It is an object of the present invention to provide a process which permits known 4-oxa-aldehydes as well as 4-oxa-aldehydes hitherto unobtainable to be prepared from the corresponding 1,3-dioxanes, the catalysts required for this purpose being readily available, having a high activity and being easy to regenerate. Furthermore, high conversions and selectivities coupled wth long catalyst lives should be ensured.

We have found that this object is achieved by a process for the preparation of 4-oxa-aldehydes of the formula (I)

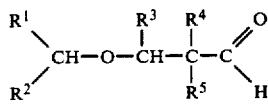

by catalytic isomerization of a 1,3-dioxane, wherein a 1,3-dioxane of the formula (II)

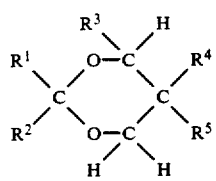

where $R^1$, $R^2$, $R^4$ and $R^5$ in formulae (I) and (II) are identical or different and are each hydrogen, a straight-chain or branched alkyl, alkenyl or alkinyl radical of not more than 18 carbon atoms, cycloalkyl or cycloalkenyl, each of 5 to 8 carbon atoms, aryl, alkylaryl, aralkyl, aralkenyl or alkenylaryl, each of 6 to 16 carbon atoms, or a heterocyclic radical, and furthermore the radicals $R^1$ and $R^2$ and/or the radicals $R^4$ and $R^5$, together with the carbon atom to which they are bonded, may form a cycloalkane, a cycloalkene or a heterocyclic structure containing 5 to 7 ring members, and the stated radicals may furthermore carry substituents which are inert under the reaction conditions, and $R^3$ is hydrogen or a straight-chain or branched alkyl radical, is isomerized using an acidic zeolite catalyst.

In the process according to the invention, the requirements set in respect of the catalysts are substantially met. In view of the prior art, the success of the process is particularly surprising since the previous approach was in precisely the opposite direction, ie. the elimination of acidic centers. It was therefore not expected that precisely zeolites possessing particularly high acidity and stringently defined structural parameters would give such excellent results within such wide limits.

The conversion of these 1,3-dioxanes to 4-oxa-aldehydes provides a good method of, for example, preparing the ethers of hydroxyneoalkanals with high selectivity and high conversion, these ethers being obtained only with difficulty, if at all, by conventional etherification methods.

The conversion may be represented by the following equation:

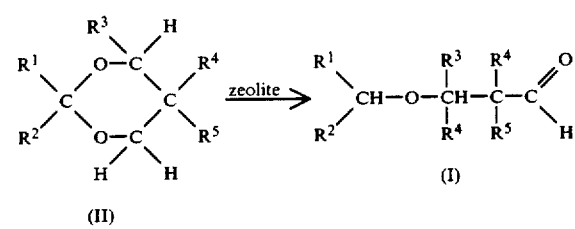

The 1,3-dioxanes of the formula (II) which are used as starting materials, and accordingly the resulting 4-oxa-aldehydes of the formula (I) contain the radicals $R^1$, $R^2$, $R^4$ and $R^5$, which are identical or different and independently of one another are each hydrogen, a straight-chain or branched alkyl, an alkenyl or alkinyl radical of not more than 18, in particular 1 to 12, preferably 1 to 6, carbon atoms, cycloalkyl or cycloalkenyl, each of 5 to 8, in particular 5 or 6, carbon atoms, aryl, alkylaryl, aralkyl, aralkenyl or alkenylaryl, each of 6 to 16, in particular 6 to 12, carbon atoms, or aromatic, saturated or unsaturated heterocyclic structures which contain one or more hetero atoms, such as nitrogen, oxygen or sulfur.

The stated radicals may furthermore carry substituents which are inert under the reaction conditions. For example, the products (I) formed from compounds (II) can in turn be converted with a diol, via an acetal of the general formula (IV)

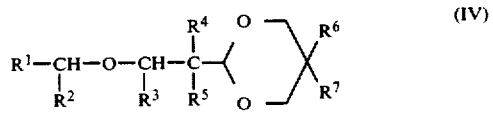

where $R^6$ and $R^7$ have the meanings given for $R^4$ and $R^5$, to give aldehydes of the formula (III)

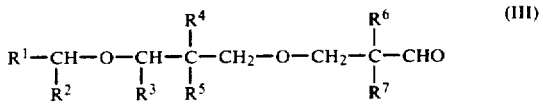

The radicals $R^1$ and $R^2$ and/or the radicals $R^4$ and $R^5$ and/or the radicals $R^6$ and $R^7$, together with the carbon atom to which they are bonded, may furthermore form a cycloalkane, cycloalkene or heterocyclic structure.

Suitable radicals $R^3$, independently of the other radicals, are hydrogen and straight-chain or branched alkyl of 1 to 12, in particular 1 to 8, preferably 1 to 4, carbon atoms.

Examples of alkyl, alkenyl and alkinyl radicals are methyl, ethyl, n-propyl, isopropyl, propenyl, isopropenyl, n-butyl, isobutyl, n-butenyl, isobutenyl, n-butynyl, pentyl, pentenyl, pentinyl, hexyl, hexenyl, heptyl, heptenyl, octyl, octenyl, nonyl, nonenyl, decyl, decenyl, dodecyl and dodecenyl. The alkyl, alkenyl and alkinyl radicals may furthermore carry substituents which are inert under the reaction conditions, eg. halogen, alkoxy, carboxyl or carboxylate.

Cycloalkyl is, for example, cyclopentyl, cyclohexyl or cycloheptyl, and cycloalkenyl is, for example, cyclopentenyl or cyclohexenyl.

Examples of suitable aromatic radicals are phenyl, benzyl, 2-phenylethyl, 3-phenylpropyl, 2-phenylpropyl, 4-phenylbutyl, 3-phenylbutyl, 2-phenylbutyl and 3-phenylbutenyl, and these radicals may or may not be further substituted by radicals which are inert under the reaction conditions.

Examples of heterocyclic and heteroaromatic radicals are tetrahydrofuran, dihydrofuran, furan, tetrahydrothiophene (thiophane), dihydrothiophene, thiophene, pyridine and thiopyran radicals. These radicals may be further substituted by radicals which are inert under the reaction conditions, such as alkyl or halogen.

Starting materials which are particularly useful for the novel process are 1,3-dioxanes in which $R^3$ is hydrogen and $R^4$ and $R^5$ are each one of the stated organic radicals.

The starting compounds of the formula (II) can be prepared by a conventional method for aldehydes or ketones or their readily cleavable derivatives, eg. dialkylketals or acetals, and 1,3-diols, in accordance with the equation below.

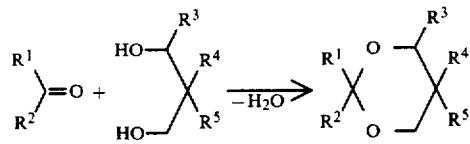

Examples of suitable diol components are propane-1,3-diol, 2-methyl-, 2-ethyl-, 2-phenyl-, 2,2-dimethyl-, 2,2-diethyl-, 2-methyl-2-ethyl-, 2-methyl-2-propyl-, 2-methyl-2-butyl-, 2-methyl-2-phenyl- and 2-ethyl-2-butylpropane-1,3-diol, 1,1-dimethylolcyclohexane and -pentane, 3,3-dimethyloltetrahydrofuran and -pyran and 2,2,4-trimethylpentane-1,3-diol.

Examples of suitable carbonyl components are aliphatic, aromatic or heterocyclic aldehydes and ketones and their acetals and ketals with low-boiling alcohols.

Examples of saturated aliphatic aldehydes are formaldehyde, acetaldehyde, propionaldehyde, butyraldehyde, pentanal, hexanal and higher homologs of n-alkanals, such as decanal, isobutyraldehyde, 2-methylbutanal, 3-methylbutanal, 3,3-dimethylbutanal, 2-methylpentanal, 2-ethylhexanal, 2-methyldecanal, glyoxal, methylglyoxal, malonaldehyde, succinaldehyde and glutaraldehyde.

Examples of heterocyclic aldehydes are tetrahydrofuran-2-carbaldehyde and -3-carbaldehyde, tetrahydrothiophene-2- and 3-carbaldehyde, 5,6-dihydropyran-6-dihydropyran-6-carbaldehyde, 2,5-dimethyl-5,6-dihydropyran-6-carbaldehyde, furan2-carbaldehyde and -3-carbaldehyde, thiophene-3-carbaldehyde and 2, 3- and 4-pyridinecarbaldehyde.

Suitable ketones are, for example, acetone, methyl ethyl ketone, diethyl ketone, methyl isopropyl ketone, diisopropyl ketone, diisobutyl ketone, methyl isobutyl ketone, methoxy-acetone, methyl vinyl ketone, methyl isopropenyl ketone, methyl isobutenyl ketone, cyclopentanone, cyclohexanone, methylcyclopentanones, methylcyclohexanones, cyclohexenone, 3,5,5-trimethylcyclohexen-2-one, methyl, ethyl and vinyl phenyl ketone, methyl furyl ketone, acetylacetone and ethyl acetoacetate.

The above compounds constitute a selection of components which can be used for the preparation of substituted 1,3-dioxanes and are not intended to restrict the range of use of the novel process to a large number of 1,3-dioxanes.

Other substituted alkanols are, for example, 3-hydroxy-2,2-dimethylpropanal (hydroxypivaldehyde), methoxy- and butoxypivaldehyde, 4-acetoxybutyraldehyde and ethyl 5-formylvalerate.

Unsaturated aldehydes, eg. acrolein, α-methylacrolein, α-ethylacrolein and higher α-alkyl-, isoalkyl- and alkenylacroleins, but-2-enal, but-3-enal, 2-methylbut-2-enal, 2-methylpent-2-enal, 2-ethylhex-2-enal, 2,2-dimethylpent-4-enal, 2-methyl-4-acetoxybut-2-enal, 2-methoxymethylacrolein, 2-(3-methoxycarbonylpropyl)-acrolein or 2-methyl-4-chlorobut-2-enal, may also be used.

Examples of aromatic aldehydes are benzaldehyde, p-methoxybenzaldehyde, phenylacetaldehyde, 2-phenyl- and 3-phenylpropanal, 2-hydroxybenzaldehyde, 3-hydroxy-4-methoxybenzaldehyde, cinnamaldehyde and benzylacrolein.

Acidic zeolite catalysts are used as catalysts for the novel conversion of 1,3-dioxanes. Zeolites are crystalline aluminosilicates which possess a highly ordered structure comprising a rigid three-dimensional network of $SiO_4$ and $AlO_4$ tetrahedra which are connected by common oxygen atoms. The ratio of Si and Al atoms to oxygen is 1:2 (cf. Ullmanns Encyclopädie d. tech. Chemie, 4th edition, volume 24, page 575 (1983)). The electrovalency of the aluminum-containing tetrahedra is compensated by inclusion of cations in the crystal, eg. an alkali metal ion or hydrogen ion. Cation exchange is possible. The voids between the tetrahedra are occupied by water molecules prior to dehydration be drying or calcination.

In the zeolites, other elements, such as B, Ga, Fe, Cr, V, As or Sb, can be incorporated in the lattice instead of aluminum, or the silicon may be replaced with a tetravalent element such as Ge.

Suitable catalysts are zeolites of the faujasite group, eg. the Y zeolite, or zeolites of the mordenite group, or fine-pore zeolites, for example those of the erionite or chabasite type. Zeolites of the pentasil type are particularly advantageous for the novel process and may have different chemical compositions. These zeolites are aluminosilicate, borosilicate, iron silicate, gallium silicate, chromium silicate, arsenic silicate, antimony silicate, bismuth silicate zeolites and mixtures of these, as well as aluminogermanate, borogermanate, gallium germanate and iron germanate zeolites and mixtures of these.

The aluminosilicate, borosilicate and iron silicate zeolites of the pentasil type are particularly useful for the isomerization according to the invention. The aluminosilicate zeolite is prepared, for example, from an aluminum compound, preferably $Al(OH)_3$ or $Al_2(SO_4)_3$, and a silicon component, preferably finely divided silica, in an aqueous amine solution, in particular in hexane-1,6-diamine, propane-1,3-diamine or triethylenetetramine solution, with or without the addition of an alkali or alkaline earth, at from 100° to 220° C. under autogenous pressure. The resulting aluminosilicate zeolites have an $SiO_2/Al_2O_3$ ratio of from 10 to 40,000, depending on the amounts of starting materials chosen. Such aluminosilicate zeolites may also be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure by reacting a boron compound, eg. $H_3BO_3$, with a silicon compound, preferably finely divided silica, in an aqueous amine solution, in particular in hexane-1,6-diamine, propane-1,3-diamine or triethylenetetramine solution, with or without the addition of an alkali or alkaline earth. Such borosilicate zeolites can also be obtained if the reaction is carried out in an ether solution, eg. diethylene glycol dimethyl ether, or in alcoholic solution, eg. hexane-1,6-diol, instead of in an aqueous amine solution.

The iron silicate zeolite is obtained, for example, from an iron compound, preferably $Fe_2(SO_4)_3$, and a silicon compound, preferably finely divided silica, in an aqueous amine solution, in particular hexane-1,6-diamine, with or without the addition of an alkali or alkaline earth, at from 100° to 220° C. under autogenous pressure.

The aluminosilicate, borosilicate and iron silicate zeolites prepared in this manner are isolated, dried at from 100° to 160° C., preferably 110° C., and calcined at from 450° to 550° C., preferably 500° C., after which they can be molded with a binder in a weight ratio of from 90:10 to 40:60, to give extrudates or tablets. Suitable binders are various aluminas, preferably boehmite, amorphous aluminosilicates having an $SiO_2/Al_2O_3$ ratio of from 25:75 to 95:5, preferably 75:25, silica, preferably finely divided silica, mixtures of finely divided $SiO_2$ and finely divided $Al_2O_3$, finely divided $TiO_2$ and clay. After the molding procedure, the extrudates or tablets are dried at 110° C. for 16 hours and calcined at 500° C. for 16 hours.

Advantageous catalysts are also obtained if the isolated aluminosilicate, borosilicate or iron silicate zeolite is molded directly after the drying procedure and subjected to calcination only after molding. The aluminosilicate, borosilicate and iron silicate zeolites prepared may also be used in pure form, without binder, as extrudates or tablets, the extrusion assistants or peptization assistants used being, for example, ethylcellulose, stearic acid, potato starch, formic acid, oxalic acid, acetic acid, nitric acid, ammonia, amines, silicoesters and graphite, or mixtures of these.

If, because of the method of preparation, the zeolite is obtained not in the catalytically active, acidic H form but, for example, in the Na form, the latter can be converted completely or partially to the desired H form by subjecting it to ion exchange, for example with ammonium ions, followed by calcination, or by treating it with an acid.

If, when the zeolite catalysts are used according to the invention, deactivation due to coking occurs, it is advisable to regenerate the zeolites by burning off the coke deposit with air or with an $air/N_2$ mixture at from 400° to 550° C., preferably 500° C. As a result, the zeolites regain their initial activity.

The activity of the catalyst can be adjusted to achieve optimum selectivity for the desired reaction product by precoking.

In order to achieve very high selectivity, high conversion and a long life, it is sometimes advantageous to modify the zeolites. A suitable method of modifying the catalysts consists in, for example, doping the unmolded zeolites with metal salts by ion exchange or by impregnation.

Particularly advantageous catalysts are obtained by doping the zeolites with transition metals such as Mo, Fe, Zn, Cu and in particular W, with noble metals, such as Pd, and with rare earth metals, such as La.

Advantageously, doping is carried out by a method in which, for example, the molded pentasil zeolite is initially taken in a riser, and, for example, an aqueous or ammoniacal solution of a halide or of a nitrate of the above metals is passed over at from 20° to 100° C. Ion exchange of this type can be carried out, for example, on the hydrogen, ammonium or alkali metal form of the zeolite. In another possible method of applying the metals to the zeolite, the zeolite material is impregnated with, for example, a halide, nitrate or an oxide of the above metals in aqueous, alcoholic or ammoniacal solution. Both ion exchange and impregnation are followed by one or more drying steps, and alternatively repeated calcination.

In a possible embodiment, for example, tungstic acid $H_2WO_4$ is dissolved completely or to a very substantial extent in water. This solution is used to impregnate the molded or unmolded zeolite for a certain time, ie. about 30 minutes. Any supernatant solution is freed from water in a rotary evaporator, after which the impregnated zeolite is dried at about 150° C. and calcined at about 550° C. This impregnation process can be carried out several times in succession in order to obtain the desired metal content.

it is also possible, for example, to prepare an ammoniacal $Pd(NO_3)_2$ solution and to suspend the pure zeolite powder in this solution at from 40° to 100° C. for about 24 hours, while stirring. The product is filtered off, dried at about 150° C. and calcined at about 500° C., and the zeolite material obtained in this manner can be further processed, with or without binders, to give extrudates, pellets or fluidizable material.

Ion exchange with the zeolites in the H form can be carried out by initially taking the zeolite in the form of extrudates or pellets in a column, and circulating, for example, an ammoniacal $Pd(NO_3)_2$ solution over the zeolite at slightly elevated temperatures of from 30° to 80° C. for from 15 to 20 hours. The product is then washed thoroughly with water, dried at about 150° C. and calcined at about 550° C.

In the case of some metal-doped zeolites, an aftertreatment with hydrogen is advantageous.

In another possible method of modification, the zeolite material, either molded or unmolded, is treated with an acid, such as hydrochloric acid, hydrofluoric acid or phosphoric acid and/or steam.

The catalysts described here can be used alternatively as extrudates, tablets or powders or in the form of fluidized catalysts. 2-4 mm long extrudates, tablets having a diameter of 3-5 mm and powders or fluidizable catalysts having particle sizes of from 0.1 to 0.5 mm are advantageously used.

The conversion according to the invention is as a rule carried out in the gas phase at from 200° to 500° C., preferably from 230° to 400° C., with a space velocity WHSV of from 0.1 to 20, preferably from 0.5 to 5, $h^{-1}$ (g of 1,3-dioxane per g of catalyst per hour). In general, the conversion increases sharply as the temperature increases, whereas the selectivity falls only slightly over a particular temperature range.

The process is carried out, as a rule, under atmospheric pressure, or under reduced or superatmospheric pressure, depending on the volatility of the starting compound. A continuous procedure is preferred.

When the conversion is complete, the resulting 4-oxa-aldehydes are isolated from the reaction mixture by a conventional method, for example by distillation. Unconverted 1,3-dioxanes (II) are, if desired, recycled to the conversion according to the invention.

The compounds obtainable by the novel process and a number of their derivatives are of interest as compouds possessing biological activity, eg. bacteriocides, and moreover are useful intermediates. For example, they can be readily converted to amines, alcohols and acids by methods familiar to the skilled worker, for example by oxidation with oxygen or by reduction, eg. by catalytic hydrogenation or hydrogenation under aminating conditions. Conversion of the novel ethers to tert-butylperoxy esters, for example by the process described in German Laid-Open Application DOS 2,922,698, provides advantageous polymerization initiators.

The Examples which follow illustrate the invention. The Comparative Examples 39 and 40 show that the catalyst described in German Laid-Open Application DOS 2,922,698 is effective only during short reaction times of from 1 to 2 hours, whereas the activity decreases virtually to zero after 4 hours.

EXAMPLES 1 TO 36

The reactions are carried out under isothermal conditions in a tube reactor (0.6 cm coil, 90 cm length) in the gas phase for not less than 6 hours. Isolation and characterization of the reaction products are carried out by conventional methods. Quantitative determination of the reaction products (I) and the starting materials (II) is carried out by gas chromatography.

The catalysts used in the Examples for the conversion of 1,3-dioxanes to 4-oxa-aldehydes are:

Catalyst A

The borosilicate zeolite of the pentasil type is prepared by hydrothermal synthesis from 640 g of finely divided $SiO_2$, 122 g of $H_3BO_3$ and 8,000 g of an aqueous hexane-1,6-diamine solution (weight ratio 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$.

This material is molded with boehmite in a weight ratio of 60:40 to give 2 mm extrudates, which are dried at 110° C. for 16 hours and calcined at 500° C. for 24 hours.

Catalyst B

Catalyst B is obtained by converting the pure borosilicate zeolite of the pentasil type (cf. preparation under catalyst A) to 2 mm extrudates with molding assistants, and drying the extrudates at 110° C. for 16 hours and calcining them at 500° C. for 24 hours.

Catalyst C

Catalyst C is prepared from an iron silicate zeolite by converting the latter to extrudates with boehmite in a weight ratio of 60:40 and then calcining the extrudates at 500° C. for 16 hours. The pentasil-type iron silicate zeolite itself is synthesized under hydrothermal conditions, under autogenous pressure and at 165° C., from 2,730 g of waterglass, dissolved in 2,530 g of an aqueous hexane-1,6-diamine solution (weight ratio 50:50), and 310 g of iron sulfate, dissolved in 210 g of 96% strength sulfuric acid and 4,250 g of water, in a stirred autoclave in the course of 4 days, after which the product is filtered off, washed thoroughly, dried at 100° C. for 24 hours and calcined at 500° C. for 24 hours. This iron silicate zeolite has an $SiO_2/Fe_2O_3$ ratio of 17.7 and a $Na_2O$ content of 0.62% by weight. These extrudates are subjected to ion exchange with 20% strength ammonium chloride solution until the product obtained by calcination at 500° C. has a residual sodium content of 0.06% by weight.

Catalyst D

Catalyst A is impregnated with an aqueous saturated $H_2WO_4$ solution for about 30 minutes, and the water in the supernatant residual solution is removed in a rotary evaporator. Thereafter, the catalyst is dried at 130° C. and calcined at 550° C. If necessary, the process is repeated until the catalyst has a W content of 4% by weight.

Catalyst E (comparative catalyst, DOS 2,922,698) 51 g of a commercial $SiO_2$ having the specification stated in German Laid-Open Application DOS 2,922,698 (eg. D 11/11 ® from BASF) is impregnated with a solution of 51 g of 0.1 N $CH_3COOH$ 3.19 g of $Pr(NO_3)_3 \cdot 5H_2O$, 3.21 g of $Nd(NO_3)_3 \cdot 5H_2O$ and 2.66 g of $CH_3COOK$, dried, and calcined at 600° C. for 4 hours.

Examples 1 to 36 describe conversions and selectivities, the type of catalyst, the chosen temperature and space velocity (WHSV) for the novel conversion of 1,3-dioxanes to 4-oxa-aldehydes. The experimental results are summarized in Table 3.

Starting materials of the formula (II)

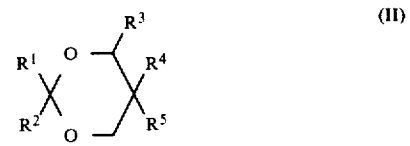

where $R^2$ and $R^3$ are each hydrogen and $R^4$ and $R^5$ are each methyl are listed in Table 1:

TABLE 1

Educts of the general formula

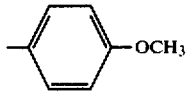

| No. | —R¹ | No. | —R¹ |
|---|---|---|---|
| I | —H | XIV | 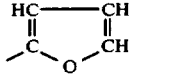 —OCH₃ |
| II | —CH₃ | XV | 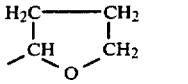 |
| III | —n-C₃H₇ | XVI | 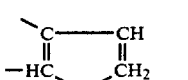 |
| IV | —i-C₃H₇ | XVII | 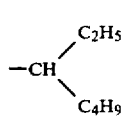 |
| V | —CH(C₂H₅)(C₄H₉) | XVIII | 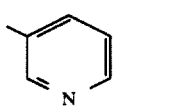 |
| VI | —CH=CH₂ | | |
| VII | —C(CH₃)₂ (—C(CH₃)(CH₃)) | | |
| VIII | —C(C₂H₅)=CH₂ | | |
| IX | —C(C₂H₅)=CH—C₃H₇ | XIX | —C(CH₃)₂CH₂OC₄H₉ |
| X | —C(CH₃)₂CH=CH₂ | XX | —(CH₂)₄—COOCH₃ |
| XI | —n-C₉H₁₉ | | |
| XII | 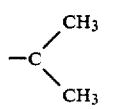 | XXI | 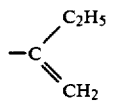 |
| XIII | 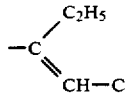 | | |

Further starting materials of the formula (II)

are listed in Table 2.

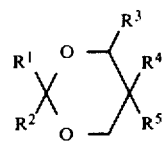     (II)

TABLE 2

Educts of the general formula

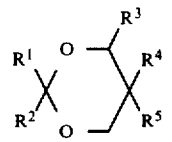

| No. | —R¹ | —R² | —R³ | —R⁴ | —R⁵ |
|---|---|---|---|---|---|
| XXII | —n-C₃H₇ | —H | —H | —CH₃ | —C₂H₅ |
| XXIII | —n-C₃H₇ | —H | —H | —CH₃ | —C₆H₅ |
| XXIV | —n-C₃H₇ | —H | —i-C₃H₇ | —CH₃ | —CH₃ |
| XXV | 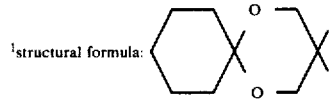 | —H | —H | —H | —H |
| XXVI | —CH₃ | —C₂H₅ | —H | —CH₃ | —CH₃ |
| XXVII¹ | —CH₂—(CH₂)₃—CH₂— | | —H | —CH₃ | —CH₃ |
| XXVIII | —CH₃ | —CH₂OCH₃ | —H | —CH₃ | —CH₃ |

¹structural formula: 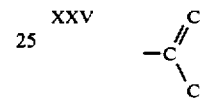

TABLE 3

| Example | Educt | Catalyst | Temperature °C. | WHSV h⁻¹ | Conversion % | Selectivity based on 4-oxa-aldehyde, % |
|---|---|---|---|---|---|---|
| 1 | I | A | 350 | 2 | 38.1 | 82.9 |
| 2 | I | B | 400 | 2.5 | 19.1 | 68.0 |
| 3 | I | C | 400 | 2 | 50.0 | 75.0 |
| 4 | I | D | 350 | 2 | 37.0 | 79.0 |
| 5 | II | B | 350 | 2 | 93.3 | 48.6 |
| 6 | II | D | 350 | 2 | 81.1 | 53.6 |
| 7 | III | B | 350 | 2 | 85 | 81.4 |
| 8 | IV | B | 250 | 1.8 | 43.5 | 91.7 |
| 9 | V | B | 250 | 2 | 22.4 | 96.0 |
| 10 | VI | B | 250 | 2 | 81.6 | 99.0 |
| 11 | VII | B | 350 | 2 | 74.5 | 81.4 |
| 12 | VII | D | 350 | 2 | 42.0 | 85.4 |
| 13 | VIII | B | 350 | 2 | 87.9 | 79.9 |
| 14 | IX | B | 300 | 3 | 85.8 | 92.8 |
| 15 | IX | D | 250 | 3 | 88.4 | 91.0 |
| 16 | X | B | 300 | 2.5 | 29.5 | 90.2 |
| 17 | XI | B | 300 | 2.5 | 100 | 69.7 |
| 18 | XII | B | 350 | 5 | 100 | 89.4 |
| 19 | XIII | B | 300 | 2.5 | 27.4 | 81.8 |
| 20 | XIV | B | 250 | 2.5 | 90.7 | 78.9 |
| 21 | XV | B | 300 | 2.2 | 67.0 | 94.8 |
| 22 | XVI | B | 300 | 2.2 | 12.3 | 82.1 |
| 23 | XVII | B | 250 | 3.5 | 58.7 | 81.1 |
| 24 | XVIII | B | 300 | 2 | 26.6 | 87.0 |
| 25 | XIX | B | 300 | 2 | 31.9 | 90.3 |
| 26 | XX | B | 250 | 3 | 18.0 | 89.4 |
| 27 | XX | B | 300 | 3 | 51.2 | 86.1 |
| 28 | XXI | D | 350 | 2 | 47.4 | 62.0 |
| 29 | XXII | B | 250 | 2.5 | 41.1 | 89.8 |
| 30 | XXII | B | 300 | 2.5 | 65.0 | 77.7 |
| 31 | XXIII | B | 300 | 3 | 57.6 | 45.0 |
| 32 | XXIV | B | 250 | 2.5 | 6.5 | 69.2 |
| 33 | XXV | B | 350 | 2 | 52.2 | 33.5 |

TABLE 3-continued

| Example | Educt | Catalyst | Temperature °C. | WHSV h$^{-1}$ | Conversion % | Selectivity based on 4-oxa-aldehyde, % |
|---|---|---|---|---|---|---|
| 34 | XXVI | B | 300 | 1.8 | 31.5 | 87.6 |
| 35 | XXVII | B | 250 | 2 | 25.7 | 94.2 |
| 36 | XXVIII | B | 250 | 2 | 54.0 | 52.1 |

EXAMPLE 37

Compound III is converted at 350° C. and a WHSV of 2 h$^{-1}$ over catalyst B in the presence of 2 l/h of N$_2$. A conversion of 85% and a selectivity of 81.4% with respect to butoxypivalaldehyde are achieved over the entire reaction time of 75 hours. As shown in Table 4, no deactivation of the catalyst is detectable during this time on stream.

TABLE 4

| Reaction time | 11 h | 29 h | 35 h | 52 h | 75 h |
|---|---|---|---|---|---|
| 4-Oxa-aldehyde* | 65.0 | 72.3 | 72.3 | 73.8 | 73.5 |

*in % by weight, based on the reacted mixture

EXAMPLE 38

A long-term experiment over 8 days with various temperature programs shows that the conversion increases sharply with increasing temperature, and the selectivity falls only at above 300° C. (Table 5). The reaction is carried out in a reactor containing 50 g of catalyst B, under isothermal conditions in a salt bath, uSing a throughput of 150 ml of 2-propyl-5,5-dimethyl-1,3-dioxane (compound III) per hour.

TABLE 5

| Temperature | 250° C. | 275° C. | 300° C. | 325° C. |
|---|---|---|---|---|
| Reaction time | 2 days | 2 days | 2 days | 2 days |
| Conversion (%) | 28 | 54 | 82 | 91 |
| Selectivity butoxypivalaldehyde (%) | 95 | 95 | 85 | 78 |

EXAMPLES 39 AND 40

Examples 39 and 40 are comparative examples using comparative catalyst E. The experimental results shown in Table 6 could only be obtained during the first two hours, since the catalyst no longer functioned after this time.

TABLE 6

| Example | Educt | Catalyst | Temperature °C. | WHSV h$^{-1}$ | Conversion | Selectivity, based on 4-oxa-aldehyde, % |
|---|---|---|---|---|---|---|
| 39 | XII | E | 300 | 2.5 | 48.9 | 77.1 |
| 40 | III | E | 250 | 2.5 | 12.6 | 13.5 |

TABLE 7

Yields and boiling points of novel compounds

| Compound | Bp./p °C./mbar | Yield of isolated product, % |
|---|---|---|

$$R-CH_2-O-CH_2-\underset{\underset{CH_3}{|}}{\overset{\overset{CH_3}{|}}{C}}-C\overset{\diagup O}{\diagdown H}$$

where R— =

TABLE 7-continued

Yields and boiling points of novel compounds

| Compound | Bp./p °C./mbar | Yield of isolated product, % |
|---|---|---|
| $H_2C=\underset{\underset{CH_3}{|}}{C}-$ | 105/90 | 58 |
| $H_2C=\underset{\underset{C_2H_5}{|}}{C}-$ | 87/15 | 69 |
| $n\text{-}C_3H_7-\underset{\underset{C_2H_5}{|}}{CH}-$ | 85/1 | 77 |
| (tetrahydrofuran-2-yl) | 96–98/5 | 62 |
| (tetrahydrothiophen-2-yl) | 92–94/1 | 50 |
| (pyridin-3-yl) | 103–106/0.6 | 21 |
| $H_3COOC-(CH_2)_4-$ | 110–112/1 | 15 |
| 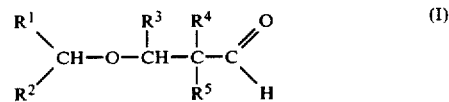 | 94/0.5 | 27 |
| 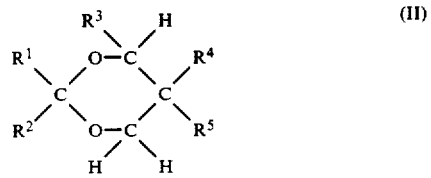 | 83–85/10 | 4 |
| $H_2C=\underset{\underset{H_5C_2}{|}}{C}-CH_2-O-(CH_2)_2-C\overset{\diagup O}{\diagdown H}$ | 74–75/12 | 15 |

We claim:
1. A process for the preparation of a 4-oxa-aldehyde of the formula

$$\underset{R^2}{\overset{R^1}{\diagdown}}CH-O-\underset{\underset{}{|}}{\overset{\overset{R^3}{|}}{CH}}-\underset{\underset{R^5}{|}}{\overset{\overset{R^4}{|}}{C}}-C\overset{\diagup O}{\diagdown H} \qquad (I)$$

which process comprises:
catalytically isomerizing a 1,3-dioxane of the formula $$\text{(II)}$$

where $R^1$, $R^2$, $R^4$ and $R^5$ in formulae (I) and (II) are identical or different and are each hydrogen, a straight-chain or branched alkyl, alkenyl or alkinyl radical of not more than 18 carbon atoms, cycloalkyl or cycloalkenyl, each of 5 to 8 carbon atoms, aryl, alkylaryl, aralkyl, aralkenyl or alkenylaryl, each of 6 to 16 carbon atoms, or a heterocyclic radical, and furthermore the radicals $R^1$ and $R^2$ and/or the radicals $R^4$ and $R^5$, together with the carbon atom to which they are bonded, may form a cycloalkane, a cycloalkene or a heterocyclic structure, and $R^3$ is hydrogen or a straight chain or branched alkyl radical, using an acid zeolite catalyst which is undoped or doped by a metal selected from the group consisting of transition metals, noble metals and rare earth metals.

2. A process as claimed in claim 1, wherein an acetal or ketal of propane-1,3-diol, of 2-methyl-, 2,2-dimethyl-, 2-methyl-2-ethyl-, 2-methyl-2-propyl-, 2-methyl-2-butyl-, 2-methyl-2-phenyl- or 1-isopropyl-2,2-dimethyl-propane-1,3-diol or of 1,1-dimethylolcyclohexane or -cyclopentane is isomerized.

3. A process as claimed in claim 1, wherein the catalyst used is a zeolite of the pentasil type.

4. A process as claimed in claim 1, wherein the catalyst used is an aluminosilicate, borosilicate or iron silicate zeolite.

5. A process as claimed in claim 1, wherein the catalyst used is a zeolite of the pentasil type which is doped with a transition metal.

6. A proceSs as claimed in claim 1, wherein the catalyst used is a tungsten-doped zeolite.

7. A process as claimed in claim 1, wherein the catalyst used is a zeolite doped with a noble metals.

8. A process as claimed in claim 1, wherein the catalyst used is a zeolite doped with rare earth metal.

9. A process as claimed in claim 1, wherein the zeolite is treated with an acid, which is hydrochloric acid, hydrofluoric acid or phosphoric acid.

10. A process as claimed in claim 1, wherein the catalyst is doped with a transition metal selected from the group consisting of molybdenum, iron, zinc, copper and tungsten.

11. A process as claimed in claim 5, wherein the catalyst is doped with a transition metal selected from the group consisting of molybdenum, iron, zinc, copper and tungsten.

12. A process as claimed in claim 5, wherein the catalyst is doped with tungsten.

13. A process as claimed in claim 1, wherein the catalytic isomerization is carried out in the gas phase at a temperature of from 200° to 500° C., and with a space velocity of from 0.1 to 20 g of 1,3-dioxane per g of catalyst per hour.

14. A process as claimed in claim 13, wherein the temperature is 230° to 400° C. and the space velocity is from 0.5 to 5 g of 1,3-dioxane per g of catalyst per hour.

15. A process as claimed in claim 1, wherein the acidic zeolite, when deactivated due to coking, is regenerated by burning off the coke deposit with air or an air/$N_2$ mixture at a temperature of from 400° to 500° C.

* * * * *

UNITED STATES PATENT AND TRADEMARK OFFICE
CERTIFICATE OF CORRECTION

PATENT NO. : 4,709,097
DATED : November 24, 1987
INVENTOR(S) : Wolfgang Hoelderich, Franz Merger and Rolf Fischer It is certified that error appears in the above-identified patent and that said Letters Patent is hereby corrected as shown below:

Claim 6, line 1: change "proceSs" to --process--.

Claim 7, line 2: change "metals" to --metal--.

Claim 8, line 2: before "rare", insert --a--.

Signed and Sealed this

Fifth Day of July, 1988

Attest:

DONALD J. QUIGG

Attesting Officer

Commissioner of Patents and Trademarks